US00PP36966P2

(12) United States Plant Patent
Fell

(10) Patent No.: US PP36,966 P2
(45) Date of Patent: Sep. 16, 2025

(54) ***ALOCASIA* PLANT NAMED 'White Dragon'**

(50) Latin Name: ***Alocasia* hybrid**
Varietal Denomination: White Dragon

(71) Applicant: David Fell, Waimanalo, HI (US)

(72) Inventor: David Fell, Waimanalo, HI (US)

( * ) Notice: Subject to any disclaimer, the term of this patent is extended or adjusted under 35 U.S.C. 154(b) by 0 days.

(21) Appl. No.: 19/183,793

(22) Filed: Apr. 19, 2025

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
CPC ..... A01H 5/12; A01H 5/00; A01H 6/10
See application file for complete search history.

(56) References Cited

PUBLICATIONS

Takano et al Pollination mutualism between *Alocasia macrorrhizos* (Araceae) and two taxonomically undescribed Colocasiomyia species (Diptera: Drosophilidae) in Sabah, Borneo, Plant Biology 14 (2012) 555-564. (Year: 2012).*

* cited by examiner

*Primary Examiner* — June Hwu
(74) *Attorney, Agent, or Firm* — James R. Holm; Plant Novelty Rights, LLC

(57) ABSTRACT

A new and distinct variety of *Alocasia* plant named 'White Dragon' particularly distinguished by its intermediate plant size, distinct dark greyish green leaf color patterning along the primary, secondary, and tertiary veins on the adaxial surface and a dominant interveinal leaf coloration of greyish yellow green to light grey on the adaxial surface; distinct interveinal leaf coloration of dark to moderate purplish pink on the abaxial surface with primary veins colored pale yellow green at the base to greyish purple from the center to the leaf apex, and secondary veins colored greyish purple; and hybrid vigor.

5 Drawing Sheets

Figure 1:
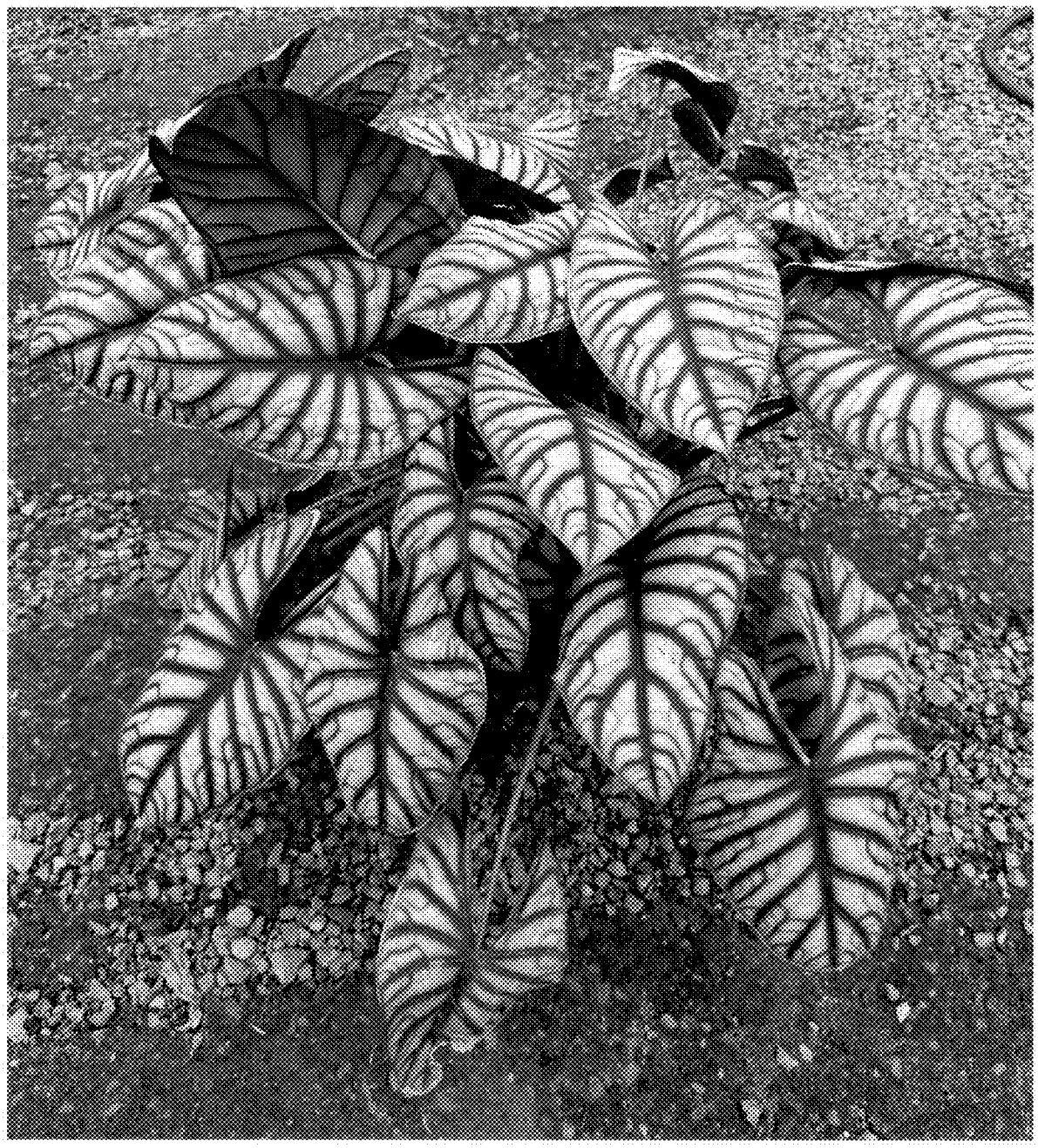

Genus and species: *Alocasia* hybrid.
Variety denomination: 'White Dragon'.

BACKGROUND OF THE NEW PLANT

The present invention comprises a new and distinct interspecific hybrid plant of *Alocasia*, hereinafter referred to by its cultivar name 'White Dragon'.

The new cultivar was derived from a breeding program conducted by the inventor at a nursery in Waimanalo, Hawaii. The overall purpose of the breeding program is to create new *Alocasia* plants with unique foliage that are durable with a good growth rate and disease and pest resistance. 'White Dragon' is the product of a controlled cross made by the inventor in February 2021 between the *Alocasia baginda* plant named 'Silver Dragon' (unpatented) as the female parent and an unnamed and unpatented *Alocasia nebula* plant as the male parent. 'White Dragon' was selected in Waimanalo, Hawaii by the inventor in August 2020 as a single unique plant from amongst progeny plants derived from said cross.

The new cultivar was selected based on its increased vigor and intermediate plant size compared to its parent plants. Plants of 'White Dragon' are larger than plants of its female parent, but smaller than plants of its male parent. 'White Dragon' was also selected due to its distinctly different leaf color patterning compared to its male parent. 'White Dragon' was first reproduced asexually by vegetative rhizome divisions in February 2022 in Waimanalo, Hawaii. Asexual propagation by vegetative rhizome divisions of the new cultivar has shown that the unique features of the new cultivar are stable and reproduce true-to-type through three successive generations.

STATEMENT REGARDING PRIOR DISCLOSURES BY THE INVENTOR

The Inventor asserts that no publications or advertisements relating to sales, offers for sale, or public distribution occurred more than one year prior to the effective filing date of this application. Any information about the claimed plant would have been obtained from a direct or indirect disclosure from the Inventor. The Inventor claims a prior art exemption under 35 U.S.C. 102(b)(1) for disclosures and/or sales that fall within a one-year grace period prior to the filing date.

SUMMARY OF THE INVENTION

The new *Alocasia* cultivar has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Alocasia* cultivar. The combination of these characteristics distinguishes 'White Dragon' as a new and distinct variety of *Alocasia:*

1. Intermediate plant size relative to its parent plants;
2. Distinct dark greyish green leaf color patterning along the primary, secondary and tertiary veins on the adaxial surface and a dominant interveinal leaf coloration of greyish yellow green to light grey on the adaxial surface;
4. Distinct interveinal leaf coloration of dark to moderate purplish pink on the abaxial surface with primary veins colored pale yellow green at the base to greyish purple from the center to the leaf apex, and secondary veins colored greyish purple; and
3. Hybrid vigor.

The new *Alocasia* cultivar 'White Dragon' can be distinguished from its male and female parents by its intermediate plant size. 'White Dragon' is larger and more vigorous than its female parent and smaller than its male parent. Additionally, when compared to the male parent, leaves of 'White Dragon' have more dark greyish green leaf color patterning along the primary, secondary, and tertiary veins on the adaxial surface. When compared to the commercial *Alocasia baginda* plant 'Silver Dragon', plants of 'White Dragon' are larger and much more vigorous. When compared to the related known cultivar 'Dragon Scale', plants of 'White Dragon' are much larger and have leaf lobes that are mostly open or separated, whereas plants of 'Dragon Scale' are much smaller and have leaf lobes that are mostly closed or fused together.

DESCRIPTION OF THE PHOTOGRAPHS

This new *Alocasia* cultivar is illustrated by the accompanying-colored photographs which show the overall appearance and distinct characteristics of the plant. The colors shown are as true as can be reasonably obtained by conventional photographic procedures. The photographs are of a 2-month-old plant divided from a 5-year-old plant and grown in an 8-inch container in a shade house in Waimanalo, Hawaii under 73 percent shade (approximately 4800-foot candles) with a temperature range of 60 to 90 degrees Fahrenheit and a humidity range of 40 to 80 percent. Colors in the photographs may differ slightly from the color values cited in the botanical description which accurately describes the colors of the new variety.

FIG. 1. shows the overall plant form and foliage of 'White Dragon'.

Figure 2:
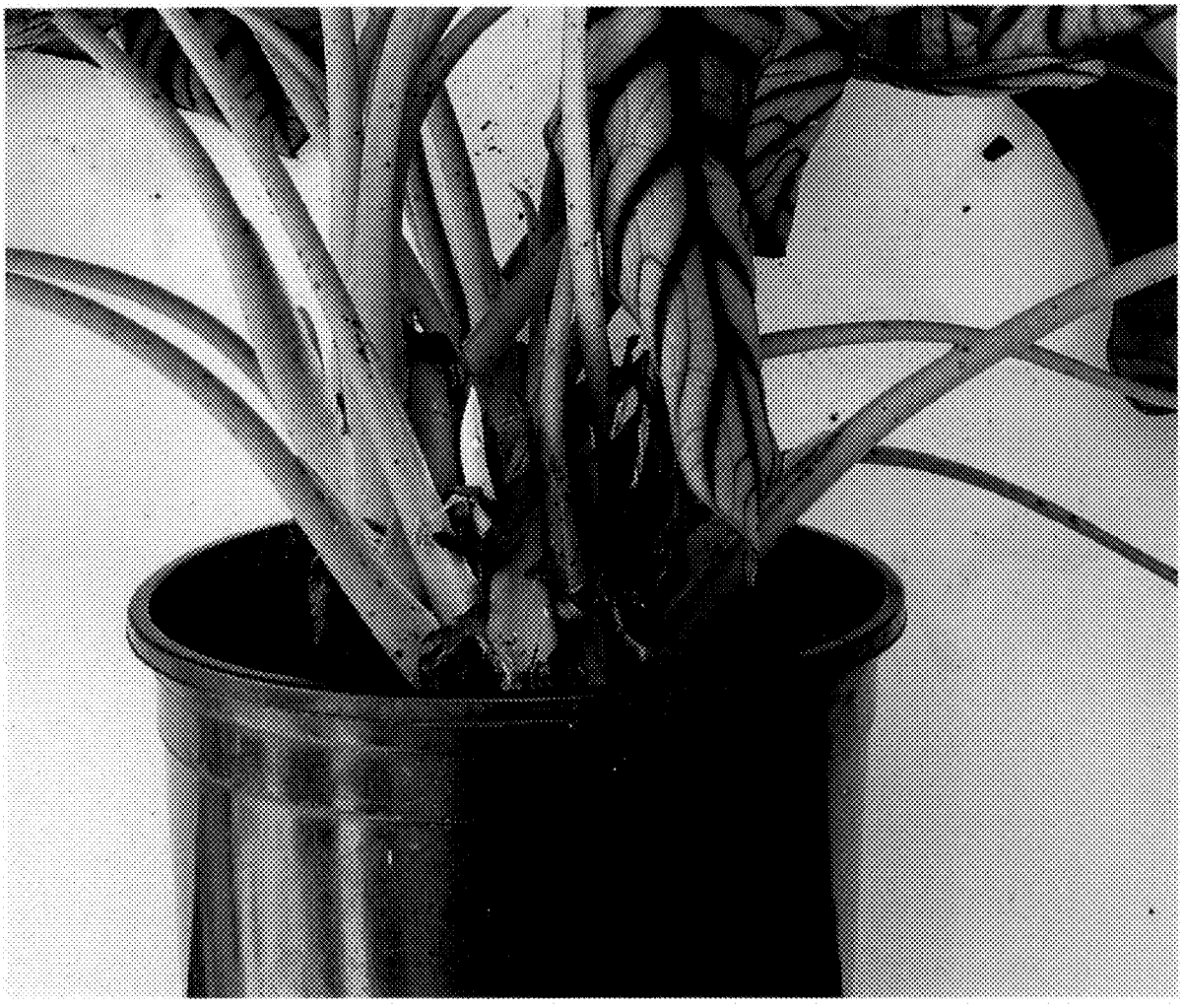

FIG. 2. shows the clumping habit of 'White Dragon'.

Figure 3:
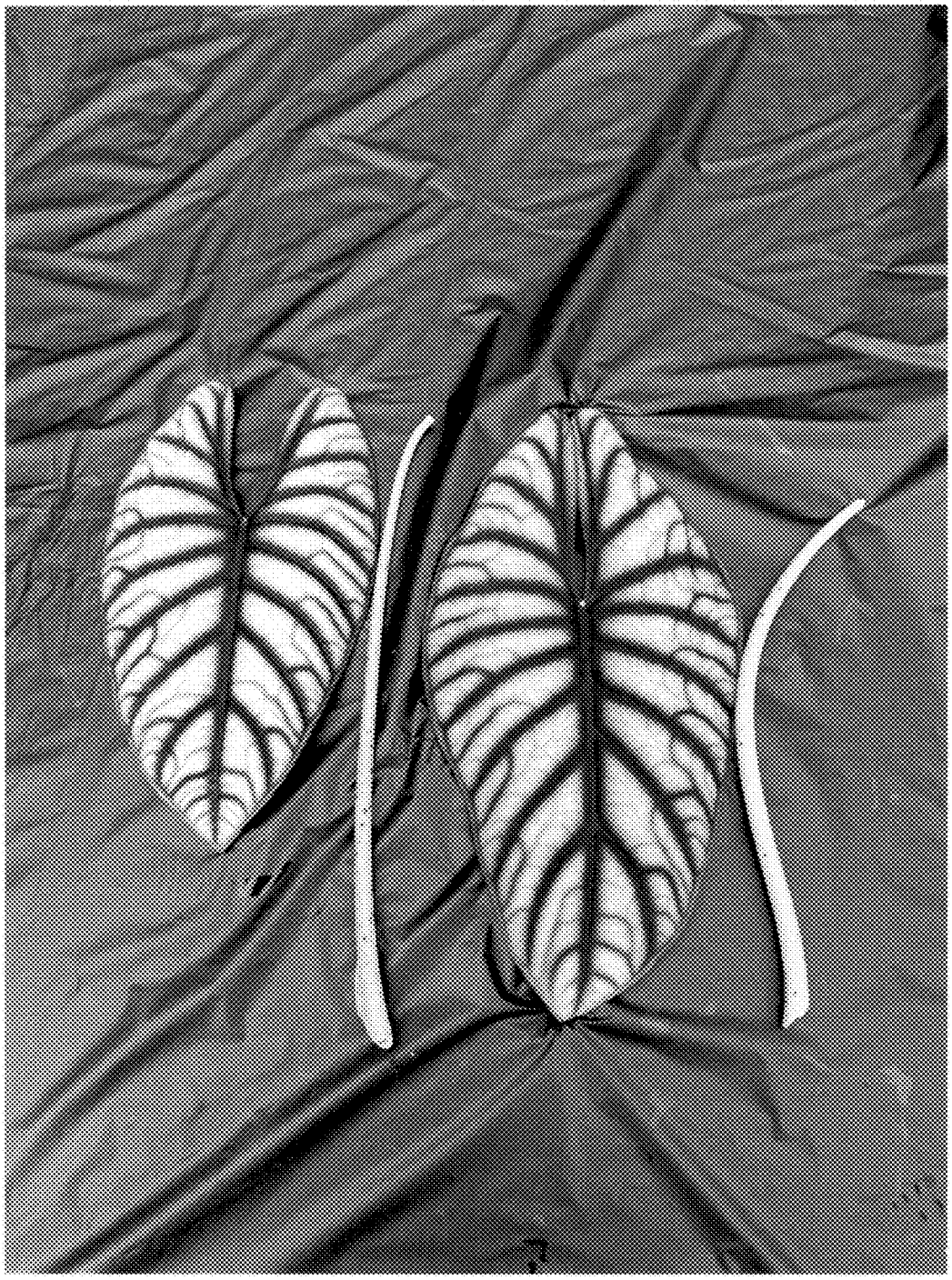

FIG. 3. shows the adaxial surface of typical mature leaves of 'White Dragon'.

Figure 4:
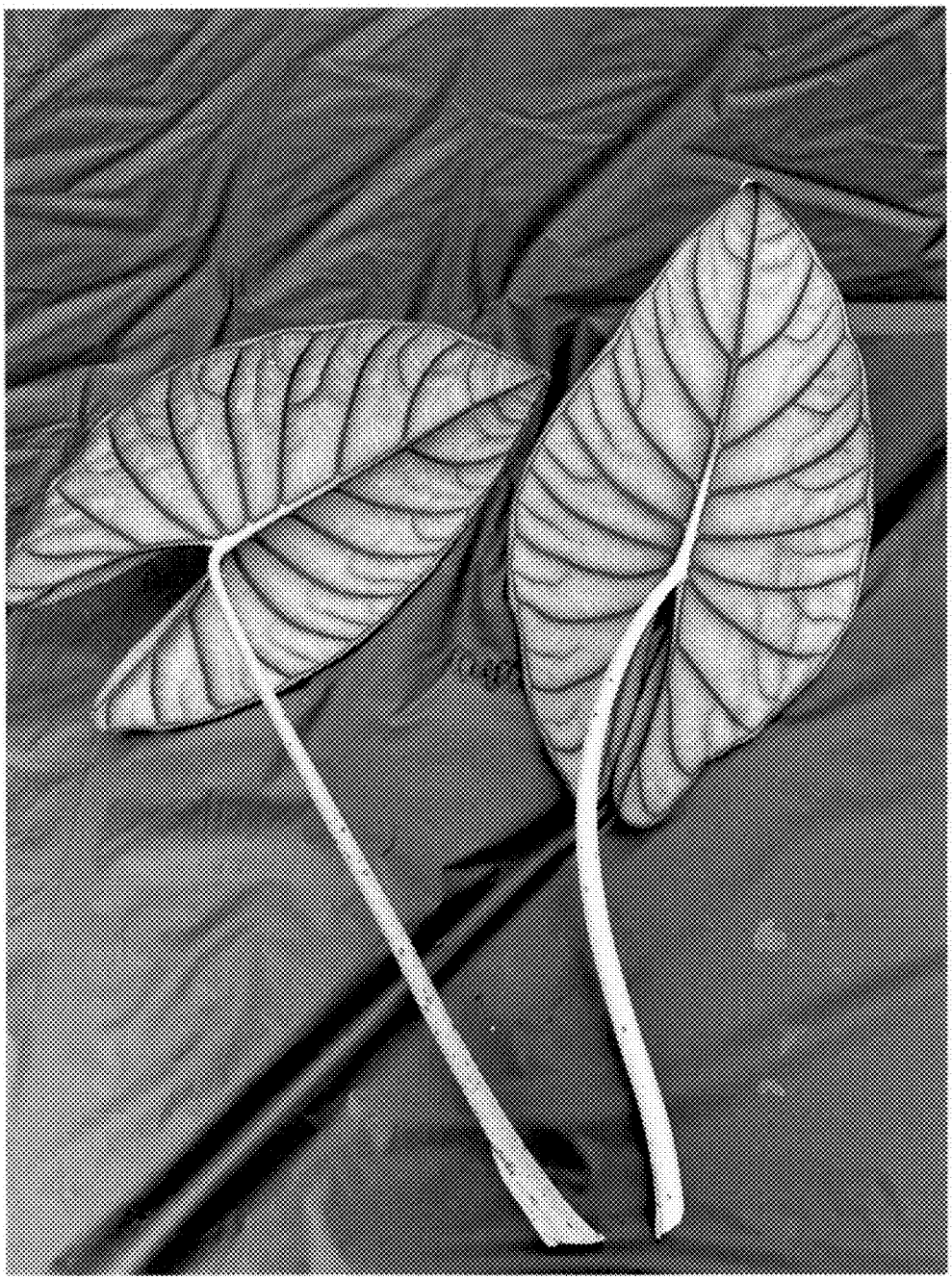

FIG. 4. shows the abaxial surface of typical mature leaves of 'White Dragon'.

Figure 5:
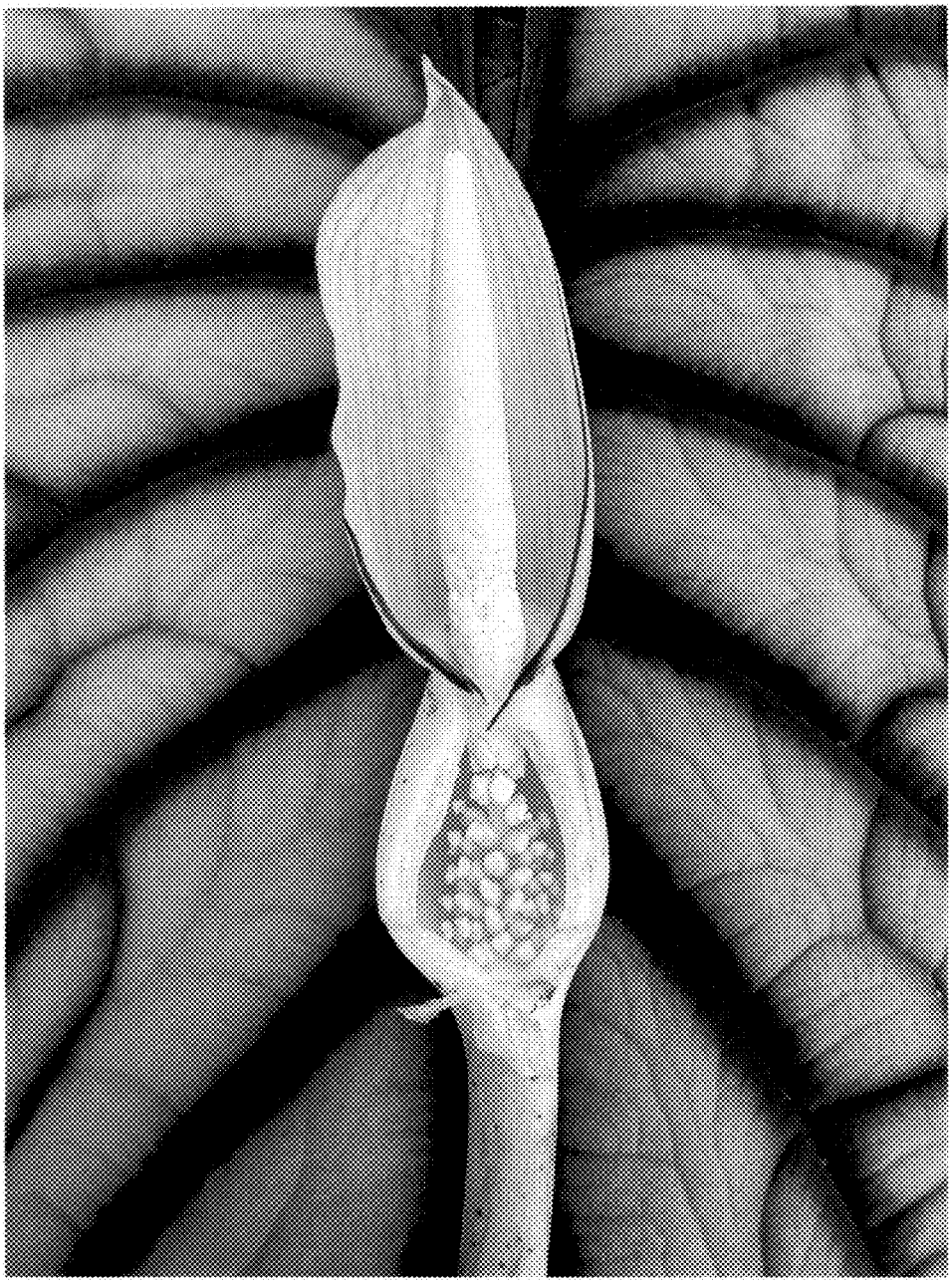

FIG. 5. shows a close up of a typical inflorescence observed on plants of 'White Dragon', with the lower part of the spathe removed to reveal the female and sterile mid zones.

DESCRIPTION OF THE NEW VARIETY

In the following description, color references are made to The Royal Horticultural Society Colour Chart, Sixth Edition, except where general color terms of ordinary dictionary significance are used.

The following observations and measurements describe plants grown under 73 percent shade (approximately 4800-foot candles) in a shade covered greenhouse in Waimanalo, Hawaii. Detailed descriptions were taken in March 2025 from a 2-month-old plant divided from a 5-year-old plant and grown in an 8-inch container. Measurements and numerical values represent averages of typical plant types.

DETAILED BOTANICAL DESCRIPTION

Classification:

*Family*.—Araceae.

*Botanical*.—*Alocasia* hybrid.

*Common*.—*Alocasia* or Elephant Ear.

*Denomination*.—'White Dragon'.

General description:

*Plant type*.—Rhizomatous tropical perennial.

*Plant habit*.—Upright and clumping with no dominant rhizomatous branch.

*Height from soil level to top of foliar plane*.—Approximately 45.0 cm.

*Plant spread*.—Approximately 115.0 cm.

*Branching characteristics*.—5 rhizomatous branches approximately 3.0 cm to 3.5 cm in diameter at the base above the soil level.

*Growth rate*.—Medium to fast.

*Propagation type*.—Vegetative rhizome divisions and meristem tissue culture.

*Roots*.—Thick, fleshy and fibrous, colored 155D (yellowish white).

Foliage description:

*Quantity of leaves per branch*.—4 to 6.

*Arrangement*.—Whorled.

*Attachment*.—Petiolate.

*Division*.—Simple.

*Cataphylls*.—Small, lance shaped, approximately 7.0 cm in length and colored 4D (pale yellow green) with specks of 183A (red) along the outside surface and 183A along the dorsal rib; cataphylls entirely surround juvenile leaves but do not persist and become brown and desiccated shortly after juvenile leaf emergence.

*Lamina*.—Shape: Sagittate. Length: Approximately 28.0 cm to 32.0 cm when measured along the center axis of the foliar plane. Width: Approximately 15.0 cm to 17.0 cm at the widest point above the lobes. Orientation: Initially held vertically and becoming horizontal when mature. Appearance: Incised venation on the adaxial surface with bullate leaf tissue between the venation. Apex: Cuspidate. Base: Sagittate. Lobes: Length: About 10.8 cm when measured from the apex of the sinus to the base of the lobe. Width: About 9.0 cm when measured at the apex of the sinus across to the edge of the lamina.

*Margins*.—Entire.

*Texture and luster* (*adaxial surface*).—Rugose, leathery and matte.

*Venation*.—Deeply incised on the adaxial surface, one primary vein (midvein) and approximately 20 secondary veins with numerous veinlets appearing in a netted pattern.

*Color* (*on mature leaves*).—Adaxial surface: Interveinal areas: Approximately 3.0 cm wide strips of N189A (dark greyish green) on and along the primary and secondary veins with narrower strips of N189A on and along the tertiary veins towards the leaf margin; a dominant color of 191B (greyish yellow green) to 191C (light grey) between the secondary veins and along the edge of the leaf margin next to the N189A (dark greyish green)

narrow strip. Basal notch: NN155D (white). Primary vein: N189A (dark greyish green). Secondary veins: N189A (dark greyish green). Tertiary veins (near the leaf margin): N189A (dark greyish green). Abaxial surface: Interveinal areas: 186C (dark purplish pink) to 186D (moderate purplish pink) and 186C to 186D at the edge of the leaf margin next to the N77A (greyish purple) narrow strip. Primary vein: 157A (pale yellow green) to 157B (pale yellow green) from the base to near the center, then N77A (greyish purple) through the center towards the apex. Secondary veins: N77A (greyish purple) with small round blisters of NN155D (white) at the intersection of the secondary veins and primary vein. Tertiary veins: (near the leaf margin): N77A (greyish purple).

*Color* (*on immature or newly expanded leaves*).—Adaxial surface: Interveinal areas: Approximately 2.5 cm wide strips of N189A (dark greyish green) with a slight overtone of 191A (greyish yellow green) along the primary and secondary veins; narrow strips of N189A with a slight overtone of 191A along the tertiary veins near the leaf margin and along the extreme edge of the leaf margin; a dominant color of 191B (greyish yellow green) to 191C (light grey) with a slight overtone of 193A (pale yellow green) between the primary and secondary veins and along the inside edge of the leaf margin. Basal notch: NN155D (white). Primary vein: N189A (dark greyish green). Secondary veins: N189A (dark greyish green). Tertiary veins (near the leaf margin): N189A (dark greyish green). Abaxial surface: Interveinal areas: 186A to 186B (moderate purplish red) and 186A to 186B along the inside edge of the leaf margin. Primary vein: 157A (pale yellow green) to 157B (pale yellow green) from the base to near the center, then N77A (greyish purple) through the center towards the apex. Secondary veins: N77A (greyish purple) with small round blisters of NN155D (white) at the intersection of the secondary veins and primary vein. Tertiary veins (near the leaf margin): N77A (greyish purple).

*Petioles*.—Strength: Flexible. Shape: Round. Aspect: Initially held upright and then arching outwards with development. Length: Approximately 33 cm to 35 cm. Diameter: Distally: 0.5 cm at point of attachment to the lamina. Proximally (above wing apex): 1.0 cm to 1.5 cm. Texture and luster: Smooth and semi glossy. Color: 144A (strong yellow green) with a moderate amount of specks colored N77A (greyish purple), specks are approximately 0.3 cm in diameter. Wings: Length: Approximately 10.0 cm. Width: Approximately 2.0 cm to 2.5 cm at the base and sharply narrowing towards the apex. Color (both inner and outer surfaces): 144A (strong yellow green).

Inflorescence:

*Type*.—Spadix surrounded by a spathe, male portion held above female portion.

*Peduncle*.—Length: 13.0 cm. Diameter: 1.4 cm, widening towards the base of the spadix, 2.0 cm. Color: Translucent, mostly 150C (yellow green) with some 157C (pale yellow green) at the base and with specks and streaks of 183C (moderate red).

*Spathe*.—Shape: Wedge-shaped above female zone, elliptic in shape surrounding female zone. Margin: Entire and undulating above female zone. Length: 9.4 cm above female zone, 3.5 cm surrounding female zone. Width: 3.5 cm above female zone; 3.5 cm surrounding female zone. Color: Above female zone: 69D (pale purple) with tints 187C (dark red) along the margin. Surrounding female zone: 157D (greenish white) with specks of 183C (moderate red) along the margin.

*Spadix*.—Length: 9.8 cm. Appendix zone: Shape: Lanceolate. Apex: Obtuse. Length: 4.7 cm. Width: 1.0 cm. Color: NN155A (yellowish white). Sterile zone: Shape: Cylindrical. Length: 1.5 cm. Width: 1.0 cm. Color: NN155B (white). Male zone: Shape: Cylindrical. Length: 1.2 cm. Width: 1.2 cm. Color: NN155B (white). Female zone: Shape: Conical. Length: 2.4 cm. Width: 1.6 cm. Color: 150C (yellow green).

Cold tolerance: None observed.

Disease and pest tolerance: Resistant to mites.

Fruit and seed set: None observed.

Drought tolerance: None observed.

What is claimed is:

1. A new and distinct variety of *Alocasia* plant named 'White Dragon', substantially as illustrated and described herein.

* * * * *